US008241922B2

(12) United States Patent
Murphy et al.

(10) Patent No.: US 8,241,922 B2
(45) Date of Patent: Aug. 14, 2012

(54) SURFACE ENHANCED RAMAN SPECTROSCOPY USING SHAPED GOLD NANOPARTICLES

(75) Inventors: Catherine J. Murphy, Columbia, SC (US); Tapan K. Sau, Chandigarh (IN); Christopher J. Orendorff, Albuquerque, NM (US); Anand M. Gole, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/026,929

(22) Filed: Feb. 14, 2011

(65) Prior Publication Data

US 2011/0137062 A1 Jun. 9, 2011

Related U.S. Application Data

(62) Division of application No. 11/721,554, filed as application No. PCT/US2005/044963 on Dec. 13, 2005, now Pat. No. 8,129,199.

(60) Provisional application No. 60/635,704, filed on Dec. 13, 2004, provisional application No. 60/648,920, filed on Feb. 1, 2005.

(51) Int. Cl.
*G01N 33/553* (2006.01)

(52) U.S. Cl. ............ 436/525; 435/4; 436/164; 436/524; 436/805

(58) Field of Classification Search ........................ None
See application file for complete search history.

(56) References Cited

U.S. PATENT DOCUMENTS

| | | | |
|---|---|---|---|
| 5,266,498 A | 11/1993 | Tarcha et al. | |
| 5,445,972 A | 8/1995 | Tarcha et al. | |
| 6,579,721 B1 * | 6/2003 | Natan et al. | 436/164 |
| 7,824,926 B1 * | 11/2010 | Porter et al. | 436/525 |
| 2003/0059820 A1 * | 3/2003 | Vo-Dinh | 435/6 |
| 2003/0157732 A1 * | 8/2003 | Baker et al. | 436/531 |
| 2003/0211488 A1 * | 11/2003 | Mirkin et al. | 435/6 |

OTHER PUBLICATIONS

Cui et al. J. Phys. Chem. B 2006, 110, pp. 4002-4006.*
Murphy et al., Room Temperature, High-Yield Synthesis of Multiple Shapes of Gold Nanoparticles in Aqueous Solution, J. Am. Chem. Soc., 2004, 126, pp. 8648-8649.

* cited by examiner

*Primary Examiner* — Chris L Chin
(74) *Attorney, Agent, or Firm* — McKee, Voorhees & Sease, P.L.C.

(57) ABSTRACT

Surface enhanced Raman scattering (SERS) spectra of 4-mercaptobenzoic acid (4-MBA) self-assembled monolayers (SAMs) on gold substrates is presented for SAMs onto which gold nanoparticles of various shapes have been electrostatically immobilized. SERS spectra of 4-MBA SAMs are enhanced in the presence of immobilized gold nanocrystals by a factor of $10^7$-$10^9$ relative to 4-MBA in solution. Large enhancement factors are a likely result of plasmon coupling between the nanoparticles (localized surface plasmon) and the smooth gold substrate (surface plasmon polariton), creating large localized electromagnetic fields at their interface, where 4-MBA molecules reside in this sandwich architecture. Moreover, enhancement factors depend on nanoparticle shape, and vary by a factor of $10^2$.

5 Claims, 9 Drawing Sheets

SURFACE ENHANCED RAMAN SPECTROSCOPY USING SHAPED GOLD NANOPARTICLES

CROSS-REFERENCE TO RELATED APPLICATIONS

This is a Divisional Application of U.S. Ser. No. 11/721,554 filed Jul. 7, 2008, which is a U.S. National Phase of PCT/US2005/044963 filed Dec. 13, 2005, which claims the benefit of U.S. Application No. 60/635,704, filed Dec. 13, 2004, and U.S. Application No. 60/648,920, filed Feb. 1, 2005, all of which are hereby incorporated herein by reference in their entireties.

ACKNOWLEDGEMENT

This invention was made with government support under Grant CHE-0336350 awarded by the National Science Foundation. The government has certain rights in the invention.

BACKGROUND

Bulk solution synthetic methods often produce nanocrystals of multiple sizes and shapes, and hence there is relatively low yield of the desired size and shape. Murphy, C. J. *Science* 2002, 298, 2139-2141. Although colloid chemists have achieved excellent control over particle size for several metallic and semiconductor systems, there has been limited success in gaining control over the shape of the nanocrystals. Schmid, G.; Ed. *Clusters and Colloids. From Theory to Applications*; VCH: New York, 1994. Watzky, M. A.; Finke, R. G., *J. Am. Chem. Soc.* 1997, 119, 10382-10400. Jana, N. R.; Peng, X., *J. Am. Chem. Soc.* 2003, 125, 14280-14281. Controlling size, shape, and structural architecture of the nanocrystals requires manipulation of the kinetic and thermodynamic parameters of the systems via utilization of various additives, light and thermal energies, and their various combinations. Ahmadi, T. S.; Wang, Z. L.; Green, T. C.; Henglein, A.; El-Sayed, M. A., *Science* 1996, 272, 1924-1925. Pileni, M. P.; Ninham, B. W.; Gulik-Krzywicki, T.; Tanori, J.; Lisiecki, I.; Filankembo, A., *Adv. Mater.* 1999, 11, 1358-1362. Li, M.; Schnablegger, H.; Mann, S, *Nature* 1999, 402, 393-395. Jin, R.; Cao, Y. C.; Hao, E.; Metraux, G. S.; Schatz, G. C.; Mirkin, C. A., *Nature* 2003, 425, 487-490. Sun, Y.; Xia, Y. *Science* 2002, 298, 2176-2179. Sun, Y.; Xia, Y., *Adv. Mater.* 2002, 14, 833-837. Sun, Y.; Mayers, B.; Herricks, T.; Xia, Y. *Nano Lett.* 2003, 3, 955-960.

Therefore, there remains a need for methods and compositions that overcome these deficiencies and that effectively provide shaped nanoparticles.

Surface enhanced Raman spectroscopy (SERS) is a powerful analytical tool for determining chemical information for molecules on metallic substrates. Moskovits, M. *Rev. Mod. Phys.* 1985, 57, 783-826. In general, there are two traditional operational mechanism to describe the overall SERS effect, electromagnetic (EM) and chemical (CHEM) enhancement mechanisms. EM enhancement is enhancement of the local electromagnetic field incident on an adsorbed molecule at a metallic surface. CHEM enhancement results from electronic resonance/charge transfer between a molecule and a metal surface, which leads to an increase the polarizability of the molecule. Otto, A.; Mrozek, I.; Pettenkofer, C. *Surf. Sci.* 1990, 238, 192. Schultz, S. G.; Janik-Czachor, M.; Van Duyne, R. P. *Surf. Sci.* 1984, 104, 419. Since the introduction of the SERS phenomenon on roughened silver electrodes, much attention has turned to SERS on spherical colloidal substrates of either gold or silver. Jeanmaire, D. L.; Van Duyne, R. P., *J. Electroanal. Chem.* 1977, 84, 1-20. Albrecht, M. G.; Creighton, J. A. *J. Am. Chem. Soc.* 1977, 99, 5215-5217. Nie, S. M.; Emery, S. R. *Science* 1997, 275, 1102-1106. Krug, J. T.; Wang, G. D.; Emory, S. R.; Nie, S. M., *J. Am. Chem. Soc.,* 1999, 121, 9208-9214. Freeman, R. G.; Bright, R. M.; Hommer, M. B.; Natan, M. J., *J. Raman Spectrosc.* 1999, 30, 733-738. Jensen, T. R.; Malinsky, M. D.; Haynes, C. L.; Van Duyne, R. P., *J. Phys. Chem. B* 2000, 104, 10549-10556. Kneipp, K.; Kneipp, H.; Deinum, G.; Itzkan, I.; Dasari, R. R.; Feld, M. S. *Appl. Spectrosc.* 1998, 52, 175-178. Colloidal nanoparticles are of interest as SERS substrates not only because they are strong light scatterers, but because of their tunable optical properties which depend on nanoparticle size, shape, and aggregation state. El-Sayed, M. A., *Acc. Chem. Res.* 2001, 34, 257-264. Kelly, K. L.; Coronado, E.; Zhao, L. L.; Schatz, G. C. *J. Phzys. Chem. B* 2003, 107, 668-677.

Spheroidal or rod-shaped nanoparticles are of significant interest as SERS substrates because of their tunable longitudinal plasmon bands and the "lightning rod" effect on surface enhancement. Schatz, G. C., *Acc. Chem. Res.* 1984, 17, 370-376. Gersten, J. I., *J. Chem. Phys.* 1980, 72, 5779-5780. While electric field enhancement is observed for 10-200 nM metallic particles, even greater local field enhancements are observed at sharp surface features, for example, at the tips of needle-shaped nanorods where the curvature radius is much smaller than the size of the nanoparticle. Gersten, J. I. *J. Chem. Phys.* 1980, 72, 5779-5780. This phenomenon is known as the lightning rod effect. Despite the desirable characteristics of metallic nanorods and nanowires as SERS substrates, only a few reports exist for SERS on rod- or wire-shaped nanoparticles. Tao, A.; Kim, F.; Hess, C.; Goldberger, J.; He, R.; Sun, Y.; Xia, Y, Yang, P. *Nano Lett.* 2003, 3, 1229-1323. Jeong, D. H.; Zhang, Y. X.; Moskovits, M., *J. Phys. Chem. B* 2004, 108, 12724-12728. Yao, J. L.; Pan, G. P.; Xue, K. H.; Wu, D. Y.; Ren, B.; Sun, D. M.; Tang, J.; Xu, X.; Tian, Z. Q. *Pure Appl. Chem.* 2000, 72, 221-228. Nikoobakht et al. have examined the use of unaggregated and aggregated gold nanorods as SERS substrates using pyridine and 4-aminothiophenol analytes. Nikoobakht, B. Wang, J. El-Sayed, M. A. *Chem. Phys. Lett.* 2002, 366, 17-23. Nikoobakht, B., El-Sayed, M. A., *J. Phys. Chem. A* 2003, 107, 3372-3378. For SERS on unaggregated nanorods, the excitation wavelength was 1064 nm, far removed from the nanorod absorption bands (~520 nm and 700 nm) where the EM enhancement mechanism is thought to be inoperative. Nikoobakht, B. Wang, J. El-Sayed, M. A. *Chem. Phys. Lett.* 2002, 366, 17-23. Despite the off-resonance condition, appreciable SERS intensity was observed with surface enhancement factors (EF) of 104 for pyridine. The authors attributed the enhancement to a chemical (CHEM) enhancement mechanism of strongly adsorbed pyridine on the Au{110} surface of these nanorods. However, no reports have been made for SERS on nanorods where the Raman excitation occurs at a wavelength that overlaps with nanorod plasmon resonance, a condition where the EM enhancement mechanism should be operative.

Large enhancement factors and even single molecule SERS have been reported for molecules at junctions between aggregated nanoparticles. Jiang, J.; Bosnick, K.; Maillard, M.; Brus, L., *J. Phys. Chem. B* 2003, 107, 9964-9972. Xu, H. X.; Bjerneld, E. J.; Kall, M.; Borjesson, L. *Phys. Rev. Lett.* 1999, 83, 4357-4360. Michaels, A. M.; Jiang, J.; Brus, L., *J. Phys. Chem. B* 2000, 104, 11965-11971. This is a result of localized surface plasmon (LSP) coupling between nanoparticles and enhanced electromagnetic field intensity localized at nanoparticle junctions. Michaels, A. M.; Jiang, J.; Brus, L., *J. Phys. Chem. B* 2000, 104, 11965-11971. Vidal, F. J. G-.; Pendry, J. B. *Phys. Rev. Lett.* 1996, 77, 1163-1166. Wang, D.-S.; Kerker, M. *Phys. Rev. B* 1981, 24, 1777-1790. Markel, V. A.; Shalaev, V. M.; Zhang, P.; Huynh, W.; Tay, L.; Haslett, T. L.; Moskovits, M. *Phys. Rev. B* 1999, 59, 10903-10909. Su, K.-H.; Wei, Q.-H.; Zhang, X.; Mock, J. J.; Smith, D. R.; Schultz, S, *Nano Lett.* 2003, 3, 1087-1090. Atay, T.; Song, J-.H.; Murmikko, A. V. *Nano Lett.* 2004, 4, 1627-1731. Fromm, D. P.; Sundaramurthy, A.; Schuck, P. J.; Kino, G.; Moemer, W. E. *Nano Lett.* 2004, 4, 957-961. This LSP coupling between aggregated gold nanorods is believed to contribute to SERS enhancement observed by El-Sayed and coworkers. Nikoobakht, B., El-Sayed, M. A., *J. Phys. Chem. A* 2003, 107, 3372-3378. It is important to note, that although it is difficult to estimate enhancement factors for aggregated nanoparticles, the authors stated that SERS enhancements were always greater for aggregated gold nanorods than for aggregated spherical nanoparticles. Nikoobakht, B., El-Sayed, M. A., *J. Phys. Chem. A* 2003, 107, 3372-3378. Similarly, LSP coupling between colloidal nanoparticles and the surface of planar substrates, referred to as surface plasmon polariton (SPP), has also been well documented and has been reported for surface plasmon resonance (SPR) spectroscopy measurements. Shchegrov, A. V.; Novikov, I. V.; Maradudin, A. A. *Phys. Rev. Lett.* 1997, 78, 4269-4272. Holland, W. R.; Hall, D. G., *Phys. Rev. B* 1983, 27, 7765-7768. Kume, T.; Nakagawa, N.; Yamamoto, K., *Solid State Commun.* 1995, 93, 171-175. Lyon, L. A.; Musick, M. D.; Natan, M., *J. Anal Chem.* 1998, 70, 5177-5183. Lyon, L. A.; Pena, D. J.; Natan, M. J., *J. Phys. Chem. B* 1999, 103, 5826-5831. Hutter, E.; Cha, S.; Liu, J-F.; Park, J.; Yi, J.; Fendler, J. H.; Roy, D., *J. Phys. Chem. B* 2001, 105, 8-12. A 20-fold increase in signal is observed for biological sandwich assays where analytes are between nanoparticles and a planar surface, and LSP-SPP coupling occurs. LSP-SPP coupling has also been observed qualitatively by Zheng et al. between silver nanoparticles and surface plasmons of planar silver substrates. Zheng, J.; Zhou, Y.; Li, X.; Ji, Y.; Lu, T.; Gu, R *Langmuir* 2003, 19, 632-636. They observed greater SERS intensity for 4-aminothiophenol (4-ATP) self-assembled monolayers (SAMs) on silver when colloidal silver nanoparticles are adsorbed to the SAM than for the 4-ATP SAM of polished and electrochemically roughened silver. Zheng, J.; Zhou, Y.; Li, X.; Ji, Y.; Lu, T.; Gu, R *Langmuir* 2003, 19, 632-636.

A significant challenge in SERS on colloidal nanoparticle substrates is determining the number of analyte molecules sampled during the experiment. It is essential to calculate not only the number of nanoparticles in solution, but also the surface coverage of analyte molecules adsorbed to these nanoparticles. This is especially difficult for nanoparticles that are synthesized using strongly adsorbed capping agents including cetyltrimethylammonium bromide (CTAB), which may or may not be displaced by the analyte of interest. Nikoobakht, B. Wang, J. El-Sayed, M. A. *Chem. Phys. Lett.* 2002, 366, 17-23. Nikoobakht, B.; El-Sayed, M. A. *Langmuir* 2001, 17, 6368-6374. In most reports, monolayer surface coverage on the nanocrystals is assumed, but if incorrect could lead to errors in calculations of EF values. For SERS on self-assembled monolayers (SAMs) on planar substrates, this problem is avoided altogether because there are no capping agents on these substrates and the number of molecules sampled is well known. Ulman, A. *Chem. Rev.* 1996, 96, 1533-1554. However, the tunability of the optical properties of planar SERS substrates is more difficult than solution-prepared colloids.

Previous research has demonstrated the high yield synthesis of gold nanorods and a plethora of other shapes of nanocrystals. Jana, N. R.; Gearheart, L. Murphy, C., *J. Adv. Mater.* 2001, 137, 1389-1393. Jana, N. R.; Gearheart, L. Murphy, C. J., *J. Phys. Chem. B* 2001, 105, 4065-4067. Sau, T. K.; Murphy, C. J. *Langmuir* 2004, 20, 6414-6420. Sau, T. K.; Murphy, C. J., *J. Am. Chem. Soc.* 2004, 126, 8648-8649. Additionally, the immobilization of CTAB-protected gold nanorods on carboxylate-terminated SAMs has been studied. Gole, A.; Orendorff, C. J.; Murphy, C. J. *Langmuir* 2004, 20, 7117-7122. In the present invention, CTAB-capped nanoparticles of various shapes are immobilized on 4-mercaptobenzoic acid (4-MBA) monolayers. SERS spectra of 4-MBA are acquired to determine the effect of immobilizing gold nanoparticles on SERS of 4-MBA SAMS on gold and to determine whether the nanoparticle shapes, specifically their optical properties and surface structure, influence SERS of 4-MBA SAMs.

Therefore, there remains a need for methods and compositions that overcome these deficiencies and that effectively provide surface enhanced Raman spectroscopy.

SUMMARY

In accordance with the purpose(s) of the invention, as embodied and broadly described herein, the invention, in one aspect, relates to methods, products, and compositions for preparing and using shaped nanoparticles. In a further aspect, the invention relates to methods, products, and compositions for surface enhanced Raman spectroscopy.

In one aspect, the invention relates to a method for enhancing a Raman signal comprising the steps of providing a sample comprising a metal surface, an analyte adhered to the surface, and a metallic nanoparticle coupled to the surface, wherein the nanoparticle has a plasmon resonance band; exposing the sample to incident energy of an excitation wavelength that overlaps with the metallic nanoparticle plasmon resonance band; and detecting the Raman signal of the analyte.

In a further aspect, the invention relates to a method for enhancing a Raman signal comprising the steps of providing a sample comprising a metal surface, a functionalized self-assembled monolayer adhered to the surface, wherein the self-assembled monolayer comprises an analyte, and a cetyltrimethylammonium bromide-capped metallic nanoparticle coupled to the surface; exposing the sample to incident energy of an excitation wavelength; and detecting the Raman signal of the analyte.

In a further aspect, the invention relates to a method for enhancing a Raman signal comprising the steps of providing a sample comprising a gold surface, a functionalized self-assembled monolayer adhered to the surface, wherein the self-assembled monolayer comprises an analyte, and a cetyltrimethylammonium bromide-capped metallic nanoparticle coupled to the surface; exposing the sample to incident energy of an excitation wavelength that overlaps with the metallic nanoparticle plasmon resonance band; and detecting the Raman signal of the analyte, wherein the Raman signal has an enhancement factor of from about $10^7$ to about $10^9$ relative to the analyte in solution.

In a further aspect, the invention relates to a composition comprising a metal surface, a functionalized self-assembled monolayer adhered to the surface, wherein the self-assembled monolayer comprises an analyte, and a cetyltrialkylammonium halide-capped metallic nanoparticle coupled to the surface.

In a further aspect, the invention relates to a method for preparing a cetyltrimethylammonium bromide-capped gold nanoparticle comprising the steps of providing a seed solution comprising a gold nanoparticle; providing an aqueous growth solution comprising cetyltrimethylammonium bromide, hydrogen tetrachloroaurate, and ascorbic acid; and adding a quantity of the seed solution to the aqueous growth solution, thereby producing a cetyltrimethylammonium bromide-capped gold nanoparticle having a shape comprising a cube, a block, a tetrapod, a sphere, a rod, a star, or a dogbone.

In a further aspect, the invention relates to the products produced by the methods of the invention.

In a further aspect, the invention relates to a cetyltrimethylammonium bromide-capped gold nanoparticle.

In a further aspect, the invention relates to a composition comprising nanoparticulate gold and a cetyltrimethylammonium bromide residue, wherein the composition has a shape comprising a cube, a block, a tetrapod, a sphere, a rod, a star, or a dogbone.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments and together with the description serve to explain the principles of the invention.

DETAILED DESCRIPTION

Figure 1:
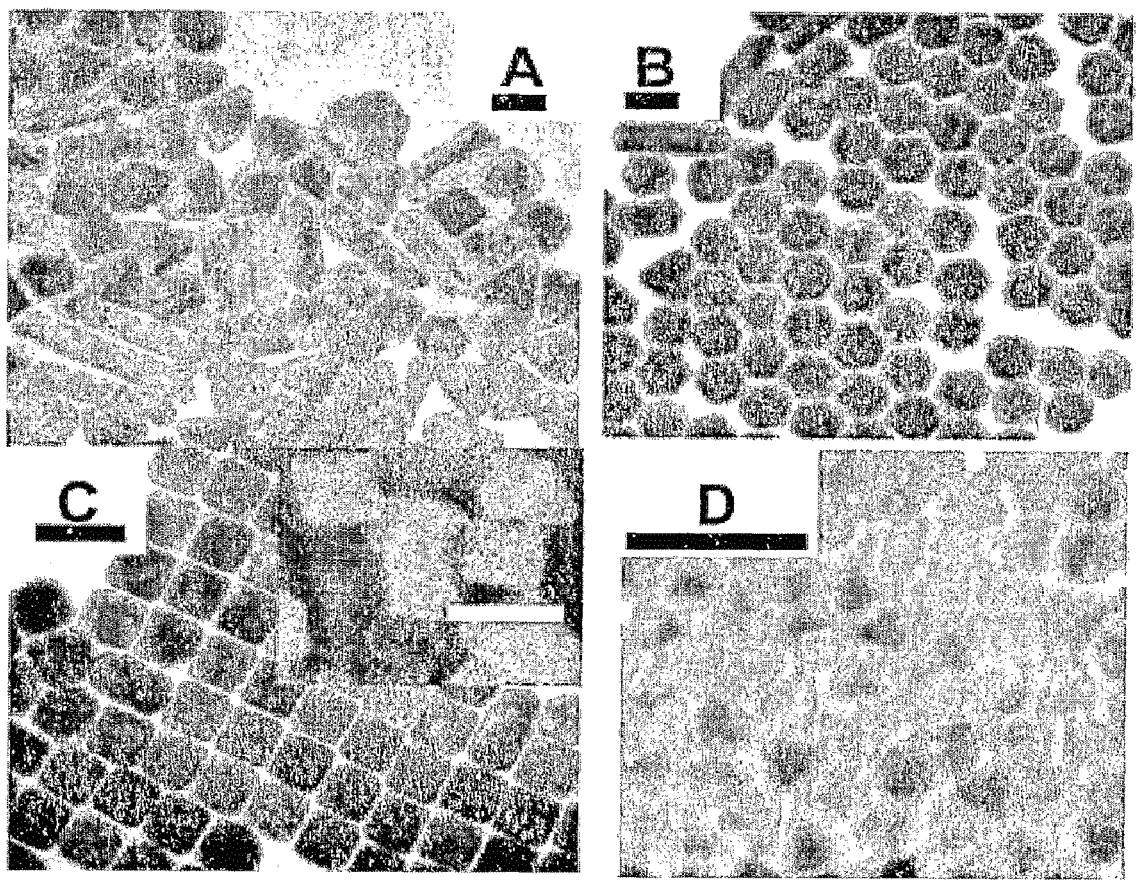
FIG. 1 shows TEM (inset SEM) images of Au nanoparticles synthesized under different conditions. AA increases from A to C; and seed concentration increases from C to D. Scale bar=100 nm. See also Table 1.

The present invention may be understood more readily by reference to the following detailed description of aspects of the invention and the Examples included therein and to the Figures and their previous and following description.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein may be different from the actual publication dates, which may need to be independently confirmed.

As used in the specification and the appended claims, the singular forms "a," "an" and "the" include plural referents unless the context clearly dictates otherwise. Thus, for example, reference to "a component," "a polymer," or "a particle" includes mixtures of two or more such components, polymers, or particles, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. SHAPED NANOPARTICLES

Various aspect ratio Ag and Au nanorods, μg nanowires, and cubic $Cu_2O$ particles in aqueous solution have been produced. Jana, N. R.; Gearheart, L.; Murphy, C. J., *J. Phys. Chem. B* 2001, 105, 4065-4067. Jana, N. R.; Gearheart, L.; Murphy, C., *J. Adv. Mater.* 2001, 13, 1389-1393. Jana, N. R.; Gearheart, L.; Murphy, C., *J. Chem. Commun.* 2001, 617-618. Gao, J.; Bender, C. M.; Murphy, C. J. *Langmuir* 2003, 19, 9065-9070. Gou, L.; Murphy, C. J. *Nano Lett.* 2003, 3, 231-234. Based upon electron diffraction analysis and high-resolution transmission electron microscopy studies, the mechanism for the evolution of cylindrical rod shapes in aqueous solution by the seeded growth method was investigated. Johnson, C. J.; Dujardin, E.; Davis, S. A.; Murphy, C. J.; Mann, S. *J. Mater. Chem.* 2002, 12, 1765-1770. Alivisatos et al., Peng et al., and Cheon et al. utilized high-temperature solution methods to obtain a score of interesting shapes for semiconductor systems. Peng, X.; Manna, L.; Yang, W. D.; Wickham, J.; Scher, E.; Kadavanich, A.; Alivisatos, A. P. *Nature* 2000, 404, 59-61. Manna, L.; Scher, E. C.; Alivisatos, A. P., *J. Am. Chem. Soc.* 2000, 122, 12700-12706. Manna, L.; Milliron, D. J.; Meisel, A.; Scher, E. C.; Alivisatos, A. P. *Nat. Mater.* 2003, 2, 382-385. Peng, Z. A.; Peng, X., *J. Am. Chem. Soc.* 2002, 124, 3343-3353. Peng, X. *Adv. Mater.* 2003, 15, 459-463. Lee, S.-M.; Jun, Y.-W.; Cho, S.-N.; Cheon, J. *J. Am. Chem. Soc.* 2002, 124, 11244-11245. Au particles with hexagonal (icosahedral) and pentagonal (decahedral) profiles have been synthesized by vapor deposition methods. Yacaman, M. J.; Ascencio, J. A.; Liu, H. B.; Gardea-Torresdey, J. *J. Vac. Sci. Technol. B* 2001, 19, 1091-1103. Yang, C. Y.; Heinemann, K.; Yacaman, M. J.; Poppa, H. *Thin Solid Films* 1979, 58, 163-168. Renou, A.; Gillet, M. *Surf Sci.* 1981, 106, 27-34. Recently, Chen et al. and Hao et al. reported the synthesis of a mixture of branched gold Au nanocrystals by using two different colloid chemical synthetic protocols. Chen, S.; Wang, Z. L.; Ballato, J.; Foulger, S. H.; Carroll, D. L. *J. Am. Chem. Soc.* 2003, 125, 16186-16187. Hao, E.; Bailey, R. C.; Schatz, G. C.; Hupp, J. T.; Li, S, *Nano Lett.* 2004, 4, 327-330.

1. Preparation Methods

In one aspect, the methods of the invention involve the preparation of Au seed particles and the subsequent addition of an appropriate quantity of the Au seed solution to the aqueous growth solutions containing desired quantities of cetyltrimethylammonium bromide (CTAB), $HAuCl_4$, ascorbic acid (AA), and, optionally, a small quantity of $AgNO_3$.

While not wishing to be bound by theory, it is believed that the morphology and dimension of the Au nanoparticles depend on the concentrations of the seed particles and CTAB, in addition to the reactants ($Au^{3+}$ and AA). All of the above factors have been found to be interdependent, thus giving rise to interesting combinations for various shapes (Table 1). For example, at $1.6 \times 10^{-2}$ M CTAB and $2.0 \times 10^{-4}$ M $Au^{3+}$ ions, nanorods, and other particles with triangular and square outlines are formed, for an AA concentration 1.6 times the $Au^{3+}$ ion concentration (FIG. 1A). On increasing the AA concentration, rod length and yield decrease, and particles with hexagonal shapes appear (FIG. 1B). Upon a further increase in AA, cube-shaped particles are formed (FIG. 1C). Simultaneous adjustment of all four reactant concentrations can produce monodisperse Au nanoparticles with hexagonal and cubic profiles in very high yield (~90%) at room temperature in aqueous solution. FIG. 1D shows that smaller particles with triangular outlines are the major product instead of cubic ones, when the seed concentration is raised, keeping other parameters the same as for the cubic shapes.

TABLE 1

| [CTAB]/M | [Au]$_{seed}$/M | [Au$_{3+}$]/M | [AA]/M | Shape/Profile | Dimension$_8$ | % Yield |
|---|---|---|---|---|---|---|
| $1.6 \times 10_{-2}$ | $1.25 \times 10_{-8}$ | $2.0 \times 10_{-4}$ | $6.0 \times 10_{-3}$ | Cube | 66 nm | ~85 |
| $1.6 \times 10_{-2}$ | $1.25 \times 10_{-8}$ | $2.0 \times 10_{-4}$ | $3.0 \times 10_{-3}$ | Hexagon | 70 nm | ~80 |
| $1.6 \times 10_{-2}$ | $1.25 \times 10_{-7}$ | $2.0 \times 10_{-4}$ | $6.0 \times 10_{-3}$ | Triangle | 35 nm | ~80 |
| $1.6 \times 10_{-2}$ | $1.25 \times 10_{-8}$ | $4.0 \times 10_{-4}$ | $6.4 \times 10_{-4}$ | Cube$_a$ | 90 nm | ~70 |
| $9.5 \times 10_{-2}$ | $1.25 \times 10_{-7}$ | $4.0 \times 10_{-4}$ | $6.0 \times 10_{-3}$ | Tetrapod$_a$ | 30 nm | ~70 |
| $1.6 \times 10_{-2}$ | $1.25 \times 10_{-8}$ | $4.0 \times 10_{-4}$ | $1.2 \times 10_{-2}$ | Star | 66 nm | ~50 |
| $5.0 \times 10_{-2}$ | $6.25 \times 10_{-7b}$ | $5.0 \times 10_{-4}$ | $3.0 \times 10_{-3}$ | Tetrapod | 293 nm | ~75 |
| $9.5 \times 10_{-2}$ | $2.5 \times 10_{-7}$ | $4.0 \times 10_{-4}$ | $6.4 \times 10_{-4}$ | Branched$_a$ | 174 nm | ~95 |

$_8$For triangular profile and cubes, this corresponds to edge lengths; for hexagonal profile, this corresponds to the distance between opposite sides; and for tetrapods and branched particles, this corresponds to center-to-tip distances. For cubes, triangles and hexagons, the dimensions are averaged over ~120 particles and are reproducible to within 5% of the given value; for the other shapes, the dimensions are averaged over ~120 particles and are within ~10% of the given value.
$_a$6.0 × 10−5M AgNO3 was used.
$_b$Seed(5) was used here, otherwise results are reported for seed(1).

2. Mechanism and Theory

Figure 2:
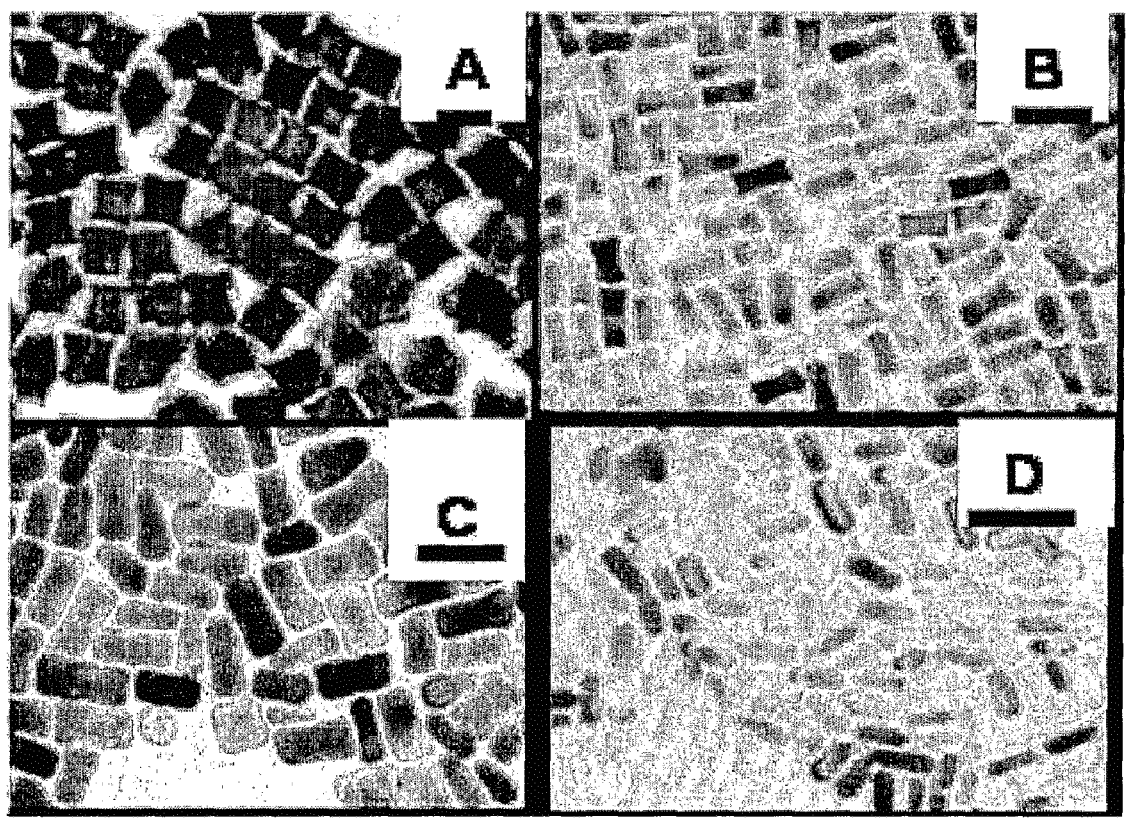
FIG. 2 shows TEM images showing cubic to rod-shaped gold particles produced with low AA concentrations in the presence of a small quantity of silver nitrate. CTAB is increased from $1.6 \times 10^{-2}$ M (A), to $9.5 \times 10^{-2}$ M (B, C, D). $Au^{3+}$ decreases from (B) to (C), whereas seed concentration increases from C to D. Scale bar=100 nm. See also Table 1.

While not wishing to be bound by theory, it is believed that the formation of various shapes is likely the outcome of the interplay between the faceting tendency of the stabilizing agent and the growth kinetics (rate of supply of Au$^0$ to the crystallographic planes). Ahmadi, T. S.; Wang, Z. L.; Green, T. C.; Henglein, A.; El-Sayed, M. A. *Science* 1996, 272, 1924-1925. Yacaman, M. J.; Ascencio, J. A.; Liu, H. B.; Gardea-Torresdey, J. *J. Vac. Sci. Technol. B* 2001, 19, 1091-1103. Yang, C. Y.; Heinemann, K.; Yacaman, M. J.; Poppa, H. *Thin Solid Films* 1979, 58, 163-168. Renou, A.; Gillet, M. *Surf. Sci.* 1981, 106, 27-34. Petroski, J. M.; Wang, Z. L.; Green, T. C.; El-Sayed, M. A. *J. Phys. Chem. B* 1998, 102, 3316-3320. For example, both fcc cubooctahedral and icosahedral particles may show hexagonal profiles under TEM. While not wishing to be bound by theory, it is believed that, as in the case of Pt$^0$-polymer systems reported by El-Sayed et al., the shape of the fine Au seeds produced in the presence of CTAB is faceted with the most stable {111} faces solvent-accessible. Petroski, J. M.; Wang, Z. L.; Green, T. C.; El-Sayed, M. A. *J. Phys. Chem. B* 1998, 102, 3316-3320. CTAB molecules appear to bind more strongly to the {100} than the {111} faces. Johnson, C. J.; Dujardin, E.; Davis, S. A.; Murphy, C. J.; Mann, S. *J. Mater. Chem.* 2002, 12, 1765-1770. Thus, lower CTAB and higher AA concentration conditions favor the faster formation and deposition of Au$^0$ onto the {111} faces, leading to their disappearance and the formation of {100} faces, thereby producing cubic shapes. Under similar (or slightly higher) CTAB concentrations and slightly lower AA concentration conditions, truncated octahedra with both {100} and {111} faces can be produced. The formation of truncated fcc shapes has also been previously observed in the presence of passivating agents for gold nanocrystals. Yacaman, M. J.; Ascencio, J. A.; Liu, H. B.; Gardea-Torresdey, J. *J. Vac. Sci. Technol. B* 2001, 19, 1091-1103. A good yield of cube-shaped particles can be obtained even at low [AA] conditions, such as for a [AA]=1.6×[Au$^{3+}$], if a small quantity of AgNO$_3$ is added to the system (FIG. 2A). These particles appear to have rough surfaces. The edge length of these particles is a function of both [Au$^{3+}$] and [seed]. However, noncubic shapes form especially upon decreasing or increasing the concentrations of Au$^{3+}$ ions. If CTAB concentration is increased from 1.6×10$^{-2}$ to 9.5×10$^{-2}$ M, a very high yield (~97%) of gold particles with rectangular outline to cylindrical rod-shapes are formed, depending on the concentration ratio of seed particles to Au$^{3+}$ ions (FIGS. 2B, C and D). Preliminary high-resolution TEM data show that the rectangular blocks are single-crystalline in structure. In electroless metal plating, reduced Ag$^+$ ions act as sacrificial seeds for the reduction of Au$^{3+}$ ions to form Au tubes/rods. Menon, V. P.; Martin, C. R. *Anal. Chem.* 1995, 67, 1920-1928. While not wishing to be bound by theory, it is believed that this mechanism is not operative in this invention, since substantially no particle formation is detected in the absence of seeds in the present experimental time scale. El-Sayed et al. have proposed that silver ions could assist in the template elongation by pairing with Br$^-$ ions of CTAB. Nikoobakht, B.; El-Sayed, M. A. *Chem. Mater.* 2003, 15, 1957-1965.

Figure 3:
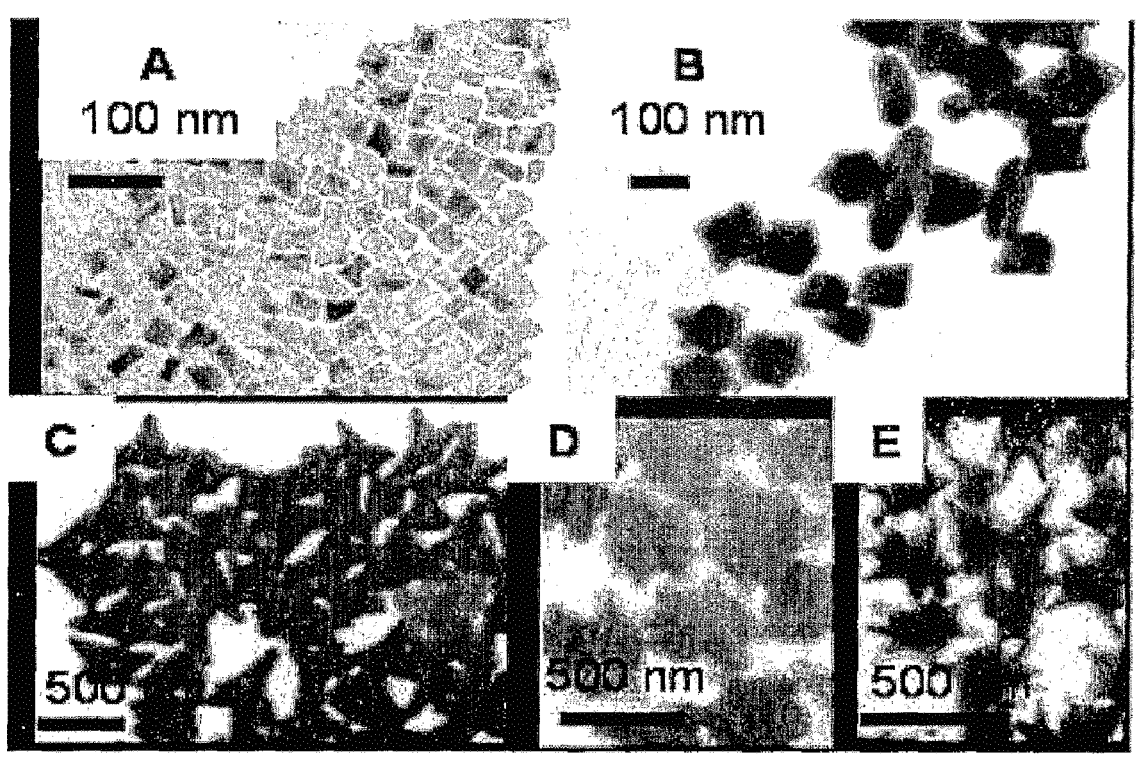
FIG. 3 shows TEM images of branched Au nanoparticles, varying in the dimension and number of branches, prepared under various combinations of [seed]/[$Au^{3+}$] ratio, and the concentrations of CTAB and AA. Tetra-pods (A), star-shape (B), larger tetra-pods (C), and multi-pods (D and E). See also Table 1.
Figure 4:
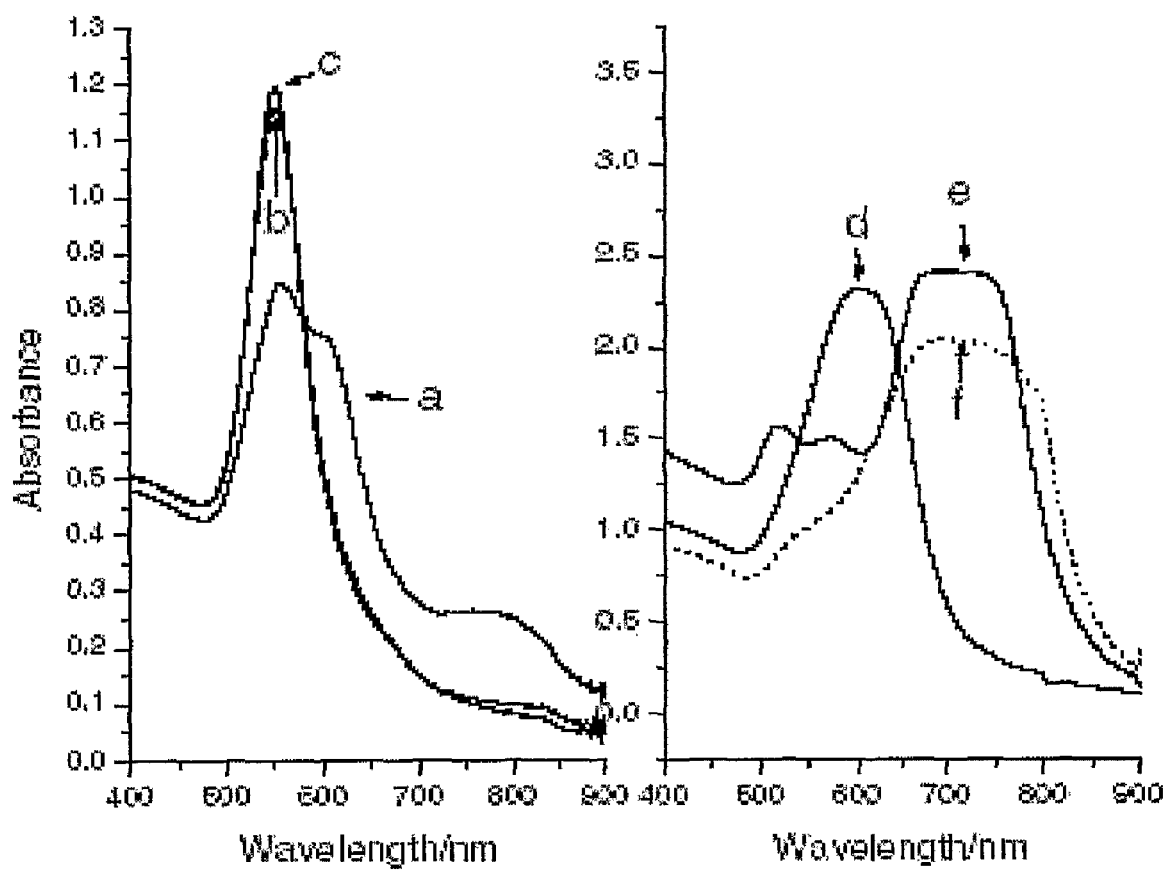
FIG. 4 shows optical absorption spectra of the solutions containing Au nanocrystals of various shapes. Solutions contain a: multiple shapes; b & c: particles with hexagonal and cubic profiles, respectively. Particle solutions correspond to the shapes given in FIGS. 1A, 1B, and 1C, respectively. d: cubic particles corresponding to that given in FIG. 2A. e: rectangular particles corresponding to that given in FIG. 2C. f: tetrapods corresponding to that given in FIG. 3A.

A lowering of the ratio of concentrations of seed to Au$^{3+}$ ions along with an increase in the concentration of AA can result in the formation of branched Au particles, depending on the concentrations of CTAB and silver nitrate (FIG. 3). However, in one aspect, silver nitrate is not essential for the branching. The yield of the branched particles produced is as high as ~70%. The four arms in larger tetrapods are clearly out of plane. The release of stress/strain effects in the growth of Au nanoparticles has been previously observed to give rise to anomalous shapes. Yacaman, M. J.; Ascencio, J. A.; Liu, H. B.; Gardea-Torresdey, J. *J. Vac. Sci. Technol. B* 2001, 19, 1091-1103. Yang, C. Y.; Heinemann, K.; Yacaman, M. J.; Poppa, H. *Thin Solid Films* 1979, 58, 163-168. Renou, A.; Gillet, M. *Surf. Sci.* 1981, 106, 27-34. However, in the case of semiconductor systems, the formation of branched structures typically requires first a relatively high supply of monomer growth units to the seed and then the evolution of branches of various kinds is determined by a balancing act between the concentration buildup and the competition of ligand/stabilizing molecules for the particle surface. Peng, X.; Manna, L.; Yang, W. D.; Wickham, J.; Scher, E.; Kadavanich, A.; Alivisatos, A. P. *Nature* 2000, 404, 59-61. Manna, L.; Scher, E. C.; Alivisatos, A. P. *J. Am. Chem. Soc.* 2000, 122, 12700-12706. Peng, X. *Adv. Mater.* 2003, 15, 459-463. Peng, Z. A.; Peng, X. *J. Am. Chem. Soc.* 2001, 123, 1389-1395. Very recently, Chen et al. also proposed that forced reduction of gold ions by ascorbic acid through the addition of NaOH is key for branching of particles. Chen, S.; Wang, Z. L.; Ballato, J.; Foulger, S. H.; Carroll, D. L. *J. Am. Chem. Soc.* 2003, 125, 16186-16187. Vis-NIR absorption spectra of the samples containing Au nanocrystals of various shapes show clear differences in optical absorption properties (FIG. 4).

The present invention, in one aspect, uses a simple solution-based seed-mediated growth method where one can controllably vary the morphology and dimension of the Au nanocrystals by the manipulation of the synthetic parameters. Moreover, these various shapes can be produced in aqueous solution at room temperature and, in one aspect, by utilizing only one surfactant, CTAB.

In one aspect, the invention relates to a method for preparing a cetyltrimethylammonium bromide-capped gold nanoparticle comprising the steps of providing a seed solution comprising a gold nanoparticle; providing an aqueous growth solution comprising cetyltrimethylammonium bromide, hydrogen tetrachloroaurate, and ascorbic acid; and adding a quantity of the seed solution to the aqueous growth solution, thereby producing a cetyltrimethylammonium bromide-capped gold nanoparticle having a shape comprising a cube, a block, a tetrapod, a sphere, a rod, a star, or a dogbone.

In one aspect, the nanoparticle has a shape comprising a cube, a block, a tetrapod, a rod with an aspect ratio of at least about 3.2, or a dogbone.

In one aspect, the providing a seed solution step comprises the step of reducing hydrogen tetrachloroaurate with ascorbic acid in the presence of cetyltrimethylammonium bromide, thereby producing seeds of less than about 4 nm. In a further aspect, the providing a seed solution step comprises the step of reducing hydrogen tetrachloroaurate with sodium borohydride in the presence of trisodium citrate, thereby producing seeds of from about 20 nm to about 30 nm.

In one aspect, the aqueous growth mixture further comprises silver nitrate.

3. Cetyltrialkylammonium Halide-Capped Nanoparticles

In one aspect, the invention relates to a cetyltrialkylammonium halide-capped nanoparticle. That is, the gold nanoparticle has at least one cetyltrialkylammonium halide residue associated with the surface of the nanoparticle. In a further aspect, the nanoparticle is a cetyltrialkylammonium halide-capped gold nanoparticle. In a further aspect, the invention relates to a cetyltrimethylammonium bromide-capped gold nanoparticle. In one aspect, the invention relates to a composition comprising nanoparticulate gold and a cetyltrimethylammonium bromide residue, wherein the composition has a shape comprising a cube, a block, a tetrapod, a sphere, a rod, a star, or a dogbone. In a further aspect, the shape comprises a cube, a block, a tetrapod, a rod with an aspect ratio of at least about 3.2, or a dogbone.

C. ENHANCING RAMAN SIGNALS

1. Methods

The methods and compositions of the invention can be used to enhance Raman signals. In one aspect, the method comprises the steps of providing a sample comprising a metal surface, an analyte adhered to the surface, and a metallic nanoparticle coupled to the surface, wherein the nanoparticle has a plasmon resonance band; exposing the sample to incident energy of an excitation wavelength that overlaps with the metallic nanoparticle plasmon resonance band; and detecting the Raman signal of the analyte.

By "coupled," it is meant that the nanoparticle is in relatively close proximity to the surface and the resulting combination can operate to enhance the vibrational spectral intensity of an analyte adhered to the surface. In one aspect, the nanoparticle and the surface can form a "sandwich" with the analyte, resulting in enhanced vibrational spectral intensity of the analyte.

By "adhered," it is meant that the analyte is associated with the surface. In one aspect, the analyte is chemically bonded to the surface by, for example, at least one covalent bond, ionic bond, coordination bond, or hydrogen bond. In a further aspect, the analyte is attracted to the surface by, for example, hydrophobic interactions or hydrophilic interactions. In a further aspect, the analyte is reversibly associated with the surface.

In a further aspect, the method comprises the steps of providing a sample comprising a metal surface, a functionalized self-assembled monolayer adhered to the surface, wherein the self-assembled monolayer comprises an analyte, and a cetyltrimethylammonium bromide-capped metallic nanoparticle coupled to the surface; exposing the sample to incident energy of an excitation wavelength; and detecting the Raman signal of the analyte. In one aspect, the nanoparticle has a plasmon resonance band and the excitation wavelength overlaps with the metallic nanoparticle plasmon resonance band. In a further aspect, the surface comprises at least one of gold, silver, copper, or silicon or a mixture or an alloy thereof. In a further aspect, the analyte comprises a thiol moiety. In a further aspect, the analyte comprises a carboxylic acid moiety. In a further aspect, the nanoparticle comprises at least one of gold, silver, or copper or a mixture or an alloy thereof.

Typically, the nanoparticle produced by the methods of the invention has a shape. In one aspect, the shape comprises a cube, a block, a tetrapod, a sphere, a rod, a star, or a dogbone. In a further aspect, the shape comprises a cube and the plasmon resonance band comprises a wavelength maximum of about 540 nm. In a further aspect, the shape comprises a sphere and the plasmon resonance band comprises a wavelength maximum of about 520 nm. In a further aspect, the shape comprises a rod with an aspect ratio of from about 3.2 to about 16 and the plasmon resonance band comprises a longitudinal wavelength maximum of from about 685 nm to about 1200 nm and a transverse maximum of about 520 nm. In a further aspect, the shape comprises a rod with an aspect ratio of greater than about 16 and the plasmon resonance band comprises a wavelength maximum of greater than about 1200 nm. In a further aspect, the shape comprises a tetrapod or a dogbone and the plasmon resonance band comprises a wavelength of about 633 nm.

In one aspect, the invention relates to a method for enhancing a Raman signal comprising the steps of providing a sample comprising a gold surface, a functionalized self-assembled monolayer adhered to the surface, wherein the self-assembled monolayer comprises an analyte, and a cetyltrimethylammonium bromide-capped metallic nanoparticle coupled to the surface; exposing the sample to incident energy of an excitation wavelength that overlaps with the metallic nanoparticle plasmon resonance band; and detecting the Raman signal of the analyte, wherein the Raman signal has an enhancement factor of from about $10^7$ to about $10^9$ relative to the analyte in solution.

a. Analyte

Those skilled in the art will recognize that there is a great deal of latitude in the composition of an analyte that yields a distinct Raman spectrum. For example, in some aspects, the analyte is a molecule. In other aspects, the analyte is not a molecule: it can be a positively or negatively charged ion (e.g., $Na^+$ or $CN^-$). If the analyte is a molecule, it can be neutral, positively charged, negatively charged, or amphoteric. The analyte can be a solid, liquid or gas. Non-molecular species such as metals, oxides, sulfides, etc. can serve as the Raman-active species. For example, a film of $SiO_2$ on Au exhibits a unique and identifiable Raman spectrum. Any species or collection of species that gives rise to a unique Raman spectrum, whether solid, liquid, gas, or a combination thereof, can serve as the analyte. Examples easily number in the many millions and include but are not limited to Hg, dimethylformamide, HCl, $H_2O$, $CN^-$, polypyrrole, hemoglobin, oligonucleotides, charcoal, carbon, sulfur, rust, polyacrylamide, citric acid, and diamond. In the case of diamond, the unique phonon mode of the particle can be used. For hemoglobin, only the porphyrin prosthetic group exhibits significant Raman activity; thus, complex substances can be used as the analyte if only part of the molecular or atomic complexity is present in the Raman spectrum.

The analyte can also be a polymer to which multiple Raman-active moieties are attached. In one aspect, the polymer can have different attached moieties yielding different Raman spectra. The polymer backbone does not necessarily itself contribute to the acquired Raman spectrum. In one aspect, the polymer can be a linear chain containing amine or ammonium groups to which Raman-active entities are attached. In a further aspect, the polymer can be a dendrimer, a branched polymer with a tightly controlled tree-like structure, with each branch terminating in a Raman-active species. A suitable dendrimer structure can have four generations of branches terminating in approximately 45 Raman-active entities.

Typically, the analyte can be any analyte known to those of skill in the art for analysis by Raman spectroscopy. In one aspect, the analyte comprises a thiol moiety. In a further aspect, the analyte comprises a carboxylic acid moiety. In a yet further aspect, the analyte comprises 4-mercaptobenzoic acid (4-MBA) or a derivative or salt thereof. In a still further aspect, the analyte comprises a portion of a functionalized self-assembled monolayer. That is, in one aspect, the analyte can be used to prepare a self-assembled monolayer on the surface.

b. Surface

Typically, the surface can be any surface known to those of skill in the art for use in Raman spectroscopy. In a further aspect, the surface comprises at least one of gold, silver, copper, or silicon or a mixture or an alloy thereof. In a yet further aspect, the surface comprises gold.

While, in one aspect, the analyte can comprise a portion of a functionalized self-assembled monolayer, in a further aspect, the surface can be functionalized with, for example, a self-assembled monolayer. In such an aspect, the self-assembled monolayer can be selected to have an affinity for an analyte, thereby providing an alternate mechanism for adhering an analyte to the surface.

c. Nanoparticle

Typically, the nanoparticle can be any nanoparticle known to those of skill in the art. In one aspect, the nanoparticles are the cetyltrialkylammonium halide-capped nanoparticles. That is, the nanoparticle has at least one cetyltrialkylammonium halide residue associated with the surface of the nanoparticle. In a further aspect, the nanoparticle comprises a cetyltrialkylammonium bromide-capped metallic nanoparticle. In a further aspect, the invention relates to a cetyltrimethylammonium bromide-capped gold nanoparticle.

In one aspect, the nanoparticle comprises at least one of gold, silver, or copper or a mixture or an alloy thereof. In a further aspect, the nanoparticle comprises gold.

In one aspect, nanoparticle has a shape comprising a cube, a block, a tetrapod, a sphere, a rod, a star, or a dogbone. In a further aspect, the shape comprises a cube and the plasmon resonance band comprises a wavelength maximum of about 540 nm. In a further aspect, the shape comprises a sphere and the plasmon resonance band comprises a wavelength maximum of about 520 nm. In a further aspect, the shape comprises a rod with an aspect ratio of from about 3.2 to about 16 and the plasmon resonance band comprises a longitudinal wavelength maximum of from about 685 nm to about 1200 nm and a transverse wavelength maximum of about 520 nm. In a further aspect, the shape comprises a rod with an aspect ratio of greater than about 16 and the plasmon resonance band comprises a wavelength maximum of greater than about 1200 nm. In a further aspect, the shape comprising a tetrapod or a dogbone and the plasmon resonance band comprises a wavelength of about 633 nm.

In certain aspects of the invention, the nanoparticles can be random aggregates of nanoparticles (colloidal nanoparticles). In other embodiments of the invention, nanoparticles can be cross-linked to produce particular aggregates of nanoparticles, such as dimers, trimers, tetramers or other aggregates. Certain alternative aspects of the invention can use heterogeneous mixtures of aggregates of different size, while other alternative aspects can use homogenous populations of nanoparticle aggregates. In certain aspects of the invention, aggregates containing a selected number of nanoparticles (dimers, trimers, etc.) can be enriched or purified by known techniques, such as ultracentrifugation in sucrose gradient solutions.

d. Excitation Energy

Typically, any source of excitation energy known to those of skill in the art can be used in connection with the invention. Suitable excitation sources include a 514.5 nm line argon-ion laser 370 from SpectraPhysics, Model 166, and a 647.1 nm line of a krypton-ion laser 370 (Innova 70, Coherent), a nitrogen laser 370 (Laser Science Inc.) at 337 nm and a helium-cadmium laser 370 (Liconox) at 325 nm (U.S. Pat. No. 6,174, 677), a light emitting diode, an Nd:YLF laser 370, and/or various ions lasers 370 and/or dye lasers 370. The excitation beam 390 can be spectrally purified with a bandpass filter (Corion) and can be focused on the Raman active substrate 240, 340 using a 6× objective lens (Newport, Model L6X). The objective lens can be used to both excite the analytes and to collect the Raman signal, by using a holographic beam splitter (Kaiser Optical Systems, Inc., Model HB 647-26N18) to produce a right-angle geometry for the excitation beam 390 and the emitted Raman signal. A holographic notch filter (Kaiser Optical Systems, Inc.) can be used to reduce Rayleigh scattered radiation. Alternative Raman detectors 380 include an ISA HR-320 spectrograph equipped with a red-enhanced intensified charge-coupled device (RE-ICCD) detection system (Princeton Instruments). Other types of detectors 380 may be used, such as Fourier-transform spectrographs (based on Michaelson interferometers), charged injection devices, photodiode arrays, InGaAs detectors, electron-multiplied CCD, intensified CCD and/or phototransistor arrays.

Typically, the excitation energy is selected so as to overlap with a plasmon band of a nanoparticle of the invention. In one aspect, the excitation energy is provided as light of an excitation wavelength incident upon the surface or upon the composition or upon the analyte. In a further aspect, the incident energy is provided by a visible light wavelength laser. In a yet further aspect, the incident energy is provided by a HeNe laser.

In one aspect, the excitation comprises visible light. In a further aspect, the excitation comprises ultraviolet light. In a further aspect, the excitation comprises infrared light. In one aspect, the excitation comprises light of a wavelength of from about 400 nm to about 500 nm, from about 500 nm to about 600 nm, from about 700 nm to about 800 nm, from about 800 nm to about 900 nm, from about 900 nm to about 1000 nm, from about 1000 nm to about 1100 nm, from about 1100 nm to about 1200 nm, or of greater than about 1200 nm. In one aspect, the excitation wavelength comprises a wavelength of about 633 nm.

e. Enhancement Factor

In one aspect, use of the methods and compositions of the invention results in enhancement of a Raman signal. The amount of enhancement can be referred to as an enhancement factor (EF). The EF can be expressed relative to an analyte in solution or an analyte on a surface. In one aspect, the Raman signal has an enhancement factor of from about $10^7$ to about $10^9$ relative to the analyte in solution.

In a further aspect, the nanoparticle has a shape comprising a cube, a block, a tetrapod, a rod with an aspect ratio of at least about 3.2, or a dogbone and the Raman signal has an enhancement factor of from about $10^1$ to about $10^2$ relative to the analyte in a sample comprising a spherical nanoparticle.

Those skilled in the art of Raman spectroscopy are aware that the general concept of inelastic light scattering has many alternative manifestations that can be used for detection. The basic "normal" Raman scattering experiment involves detection/measurement of Stokes-shifted photons, i.e., those with a lower energy than the incident photons. Anti-Stokes photons—those with energies greater than the incident photons—are also generated in a Raman experiment. While the intensity of anti-Stokes Raman bands is typically low compared to the Stokes bands, they offer one very significant advantage: the lack of interference from fluorescence, which by definition occurs at lower energies than excitation. In embodiments in which the overall SERS intensity is sufficiently high, this may be an attractive method for detection.

For molecules whose absorption spectrum overlaps with the laser excitation wavelength, Raman experiments can be said to be in resonance; both the theory and practice of resonance Raman are well understood. SERS experiments carried out under these circumstances can also be referred to as SERRS (surface enhanced resonance Raman scattering). SERRS spectra are typically more intense than normal Raman spectra, and may provide an additional benefit. Organic molecules that possess high extinctions in the visible region of the spectrum also exhibit relatively complex molecular structures, and as such might not be optimal choices for the intermediate layer. On the other hand, coordination complexes can have reasonably high absorptivity and still possess simple structures. For example, simple homoleptic complexes of Cu(I) and Cu(II) are often intensely colored (e.g., $[Cu(NH_3)_4]^-$).

In addition to SERS and SERRS, there are a variety of other detection mechanisms contemplated by the instant invention, including but not limited to surface enhanced infrared absorption spectroscopy (SEIRA), surface enhanced hyperRaman spectroscopy (SEHRS), and its resonant analog, SEHRRS. In SEHRS and SEHRRS, two photons of frequency A generate a scattering event at a frequency of 2 A. The primary benefit of this method is the total lack of interference by fluorescence or any other background process: one can excite a particle with 800 nm light and observe photons Raman-shifted from 400 nm. In general, for a given analyte with N atoms, there are either 3N-5 or 3N-6 unique vibrations; all of these vibrations can be found in either the Raman, hyperRaman, or infrared spectrum. Indeed, in some aspects, identification can rest on a combination of optical interrogation methods, including methods that rely on inelastic scattering of photons (e.g., SERS, SERRS, SEHRS, and SEHRRS, in both Stokes and anti-Stokes modes), methods that rely on elastic scattering of photons (e.g., Raleigh scattering and hyperRaleigh scattering for particles with dimensions at least 1/10th of the excitation wavelength), and methods that rely on adsorption, e.g., SEIRA.

2. Compositions

Typically, various compositions of the invention can be used in connection with the methods of the invention. In one aspect, the invention relates to a composition comprising a metal surface, a functionalized self-assembled monolayer adhered to the surface, wherein the self-assembled monolayer comprises an analyte, and a cetyltrialkylammonium halide-capped metallic nanoparticle coupled to the surface. In one aspect, the surface comprises at least one of gold, silver, copper, or silicon or a mixture or an alloy thereof. In a further aspect, the nanoparticle comprises a cetyltrialkylammonium bromide-capped metallic nanoparticle. In a further aspect, the nanoparticle comprises a cetyltrimethylammonium bromide-capped metallic nanoparticle.

D. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Preparation of Shaped Nanoparticles a. General Procedures

In a typical seed synthesis, a 10 mL solution of Au seeds is prepared by the reduction of $HAuCl_4 \cdot 3H_2O$ (2.5×10-4 M) by ice-cold $NaBH_4$ (6.0×10-4 M) in the presence of cetyltrimethylammonium bromide (CTAB, 7.5×10-2 M). The $NaBH_4$ solution is added at a time to the solution containing CTAB and $HAuCl_4$ and the reaction mixture is then shaken (or magnetically stirred) for two minutes allowing the escape of the gas formed during the reaction. These seeds are likely four nm or smaller in diameter and are designated as seed (1).

Au seeds are produced at two other CTAB concentration conditions also, namely $9.5 \times 10^{-2}$ M and $5.0 \times 10^{-2}$ M. One can produce various shapes using these two seeds as well. However, the amounts of seed particles and AA required for a given $Au^{3+}$ ion and CTAB concentration are different for each of them.

The same is true for a seed sample produced from $1.0 \times 10^{-4}$ M $HAuCl_4$ solution. Relatively large seeds (20-30 nm in diameter) were also prepared by the reduction of the same quantity of $HAuCl_4$ ($2.5 \times 10^{-4}$ M) by ascorbic acid ($4.0 \times 10^{-4}$ M) in the presence of tri-sodium citrate ($2.5 \times 10^{-4}$ M) as stabilizer and designated these seeds as seed (5). Cylindrical rod-shaped and armed Au particles were produced in high yield by using these larger seed particles. All the seeds' are used between 2 and 24 hours after their preparation.

In a typical growth reaction, 0.20 mL $HAuCl_4$ solution is added to 4.75 mL CTAB solution (0.10 M) followed by the addition of 0.03 mL $AgNO_3$ (0.01 M), 0.032 mL L-ascorbic acid (0.10 M), and 0.01 mL Au seed solutions. The solution is gently mixed by inversion of the test tube after the addition of every component.

b. TEM Studies

TEM images are obtained by Hitachi H-8000 or JEOL JEM-100CXII electron microscope. Typically 1.5 mL of the solution is centrifuged for 10 min at a speed of 10000 rpm to precipitate the solid. The supernatant is discarded. Then, the solid residue is redispersed in 1.5 mL DI water and centrifuged again. Finally the solid residue is redispersed in a suitable volume of DI water depending on the quantity of the residue. 7 μL of this solution is dropcast on a TEM grid and allowed to dry in open atmosphere.

c. Role of Silver Nitrate

Rods of cylindrical shape and penta-twinned structure and higher length along with a substantial number of spherical particles are formed when silver nitrate is not used in the system. Preliminary studies show that single crystalline rods are formed in the presence of silver nitrate. In the presence of silver nitrate, transverse growth typically occurs more and the seeds hardly form spherical particles. EDAX studies show that 3 to 7 wt % of silver is associated with the particles. It can be present as alloyed $Ag^0$ in the particle or as adsorbed $Ag^+$ on the particle surface.

2. Surface Enhanced Raman Spectroscopy

A. NANOSHAPE SYNTHESIS

Gold nanoparticles including cubes (edge length=61±3 nm), blocks (aspect ratio 2.4±0.4, length=81±9 nm, width=34±3 nm), tetrapods (center width=81±18 nm, edge length=107±18 nm), spheres (diameter=29±6 nm), and rods, aspect ratio 3.2±0.6 (length=55±7 nm, width=17±3 nm), 4.4±0.9 (length=62±6 nm, width=14±3 nm), and 16.0±5.3 (length=372±119 nm, width=23±4 nm), are prepared using the above procedure. "Dogbone"-shaped gold nanoparticles (center width=21±2 nm, end width=30±4 nm, length=68±11 nm) are prepared by adding 10 mL of as-prepared gold nanorods (aspect ratio 4.4) to a growth solution containing 8.5 mL of 0.1 M CTAB, 0.5 mL of 0.01 M $HAuCl_4$, and 1.0 mL of 0.1 M ascorbic acid. The unstirred solution changes color from tan to dark blue in ~2 minutes and is stored at room temperature for >2 hours prior to use.

B. NANOPARTICLE IMMOBILIZATION OF SELF-ASSEMBLED MONOLAYERS

Gold substrates are prepared by sputtering 10 nm of chromium, followed by 100 nm of gold, on piranha-cleaned glass microscope slides. 4-MBA self-assembled monolayers (SAMs) are formed by immersing the gold-coated glass slides, cut to 1 $cm^2$, into a 1 mM ethanolic solution of 4-MBA for 24 hrs, rinsed thoroughly with ethanol, and dried with nitrogen. CTAB-protected nanoparticles are immobilized onto 4-MBA SAMs using a similar protocol described previously for the immobilization of gold nanorods on 16-mercaptohexadecanoic acid (16-MHA) SAMs. See Gole, A.; Orendorff, C. J.; Murphy, C. J. *Langmuir* 2004, 20, 7117-7122. Briefly, 10 mL of as-prepared nanoparticles are centrifuged at various speeds depending on nanoparticle size (7,000-14,000 RPM) and the pellet is redispersed in 1 mL of deionized water to remove excess surfactant in the supernatant. After two centrifugation steps, 1 mL of nanoparticle solution is diluted to 3 mL with deionized water. The 4-MBA SAMs on gold-coated glass substrates are immersed in the resulting aqueous nanoparticle solutions for 3 hours. Substrates are rinsed with deionized water and dried with nitrogen. Under these conditions, the 4-MBA SAM is deprotonated, allowing for electrostatic binding of the cationic CTAB-capped gold nanocrystals.

C. INSTRUMENTATION

Surface enhanced Raman spectra are collected using a Detection Limit Solution 633 Raman system using a 633 nm helium neon laser with 25 mW laser power at the sample. Integration times are given in the figure captions for each spectrum. Spectra are corrected for background using GRAMS 32 software (Galactic). Absorption spectra are acquired using a CARY 500 Scan UV-vis-NIR spectrometer. Scanning electron micrographs are acquired using an FEI Quanta 200 environmental scanning electron microscope. Various magnifications are used and are provided in the figure captions. Raman spectra and SEM images are acquired on the same sample in approximately the same region in order to minimize possible effects from sample heterogeneity. Transmission electron microscopy is performed on either a Hitachi H-8000 or a JEOL 100CXII instrument.

D. RESULTS

Figure 5:
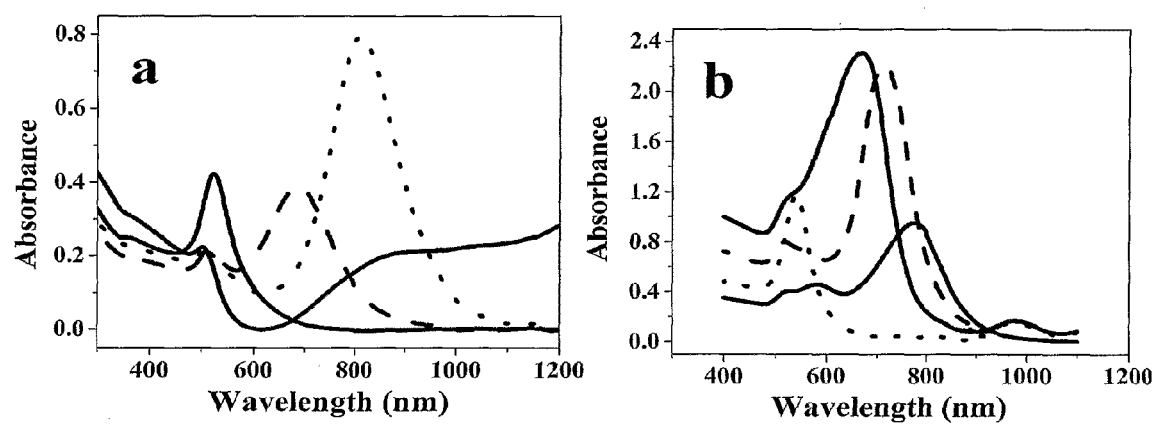
FIG. 5 shows UV-vis-NIR absorption spectra of (a) spheres (--), aspect ratio 3.2 rods (- - - - -) aspect ratio 4.4 rods (. . . . .) aspect ratio 16 rods (--), (b) dogbones (--), cubes (. . . . .) tetrapods (--), and blocks (- - - - -).

Nanoparticle plasmon resonance and immobilization. FIG. 5 shows absorption spectra of gold nanoparticles of various shapes, including rods, cubes, dogbones, tetrapods, and blocks. Cubes and spheres have only one plasmon band at ~540 and ~520 nm, respectively. Rod-shaped nanoparticles have plasmon bands corresponding to both transverse and longitudinal absorption, where the wavelength of longitudinal absorption increases with aspect ratio, from 685 nm for aspect ratio 3.2 rods to >1200 nm for aspect ratio 16 rods. Dogbones, tetrapods, and blocks have multiple plasmon bands from 525 to 775 nm corresponding to the variable dimensions along multiple axes of these particles.

Aspect ratio 3.2 nanorods, tetrapods, and dogbones have significant plasmon absorption overlap with the HeNe laser excitation source used in our SERS experiments (632.8 nm). Resonance between the incident radiation and the electronic absorption maxima should contribute to greater SERS enhancement for these nanoparticles than those without appreciable absorption at 632.8 nm. Other chemical effects of these nanoparticles can contribute to large SERS enhancements, including the surface free energy of the nanocrystals and radius of curvature of the nanoparticle features (i.e., lightning rod effect).

The utility of both SEM and AEM has been demonstrated in imaging aspect ratio 18 nanorods immobilized on 16-MHA monolayers. Gole, A.; Orendorff, C. J.; Murphy, C. J. *Langmuir* 2004, 20, 7117-7122. For nanoparticles <100 nm in size and in various of shapes, AFM can be an ideal technique for imaging them on surfaces, as its lateral resolution is superior to that of SEM. However, imaging these surfaces in contact or in tapping mode AFM typically perturbs the monolayer-nanoparticle architecture by moving nanoparticles on the surface with the AFM tip. While not wishing to be bound by theory, it is believed that this is likely a consequence of the smaller particle sizes employed herein; there is less surface area in contact with the SAM, leading to fewer favorable electrostatic interactions between nanoparticles and the underlying substrate. Therefore, scanning electron micrographs can be acquired for immobilized nanoparticles in order to calculate nanoparticle density.

Figure 6:
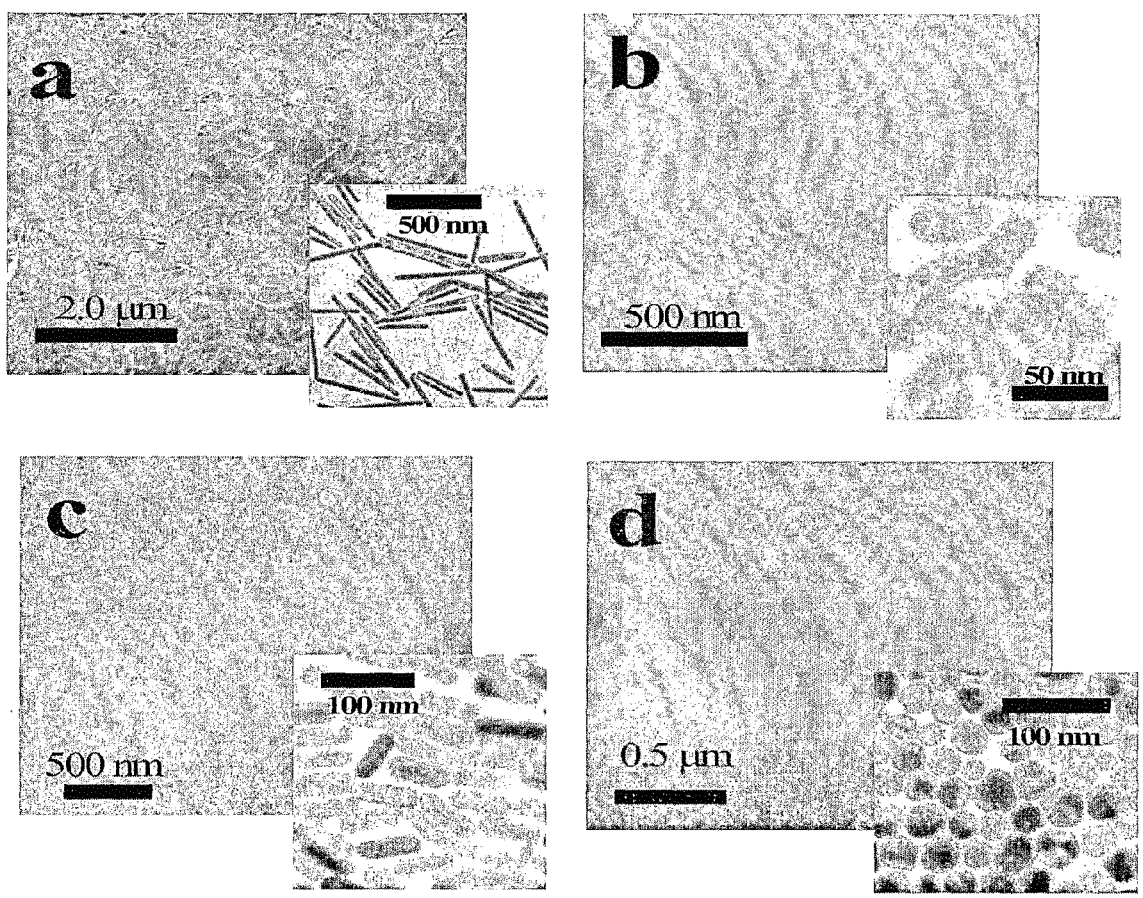
FIG. 6 shows SEM and TEM (inset) images of (a) aspect ratio 16 rods, (b) aspect ratio 3.2 rods, (c) aspect ratio 4.4 rods, (d) spheres, (e) tetrapods, (f) dogbones, (g) cubes, and (h) blocks immobilized on 4-MBA SAMs.
Figure 6:
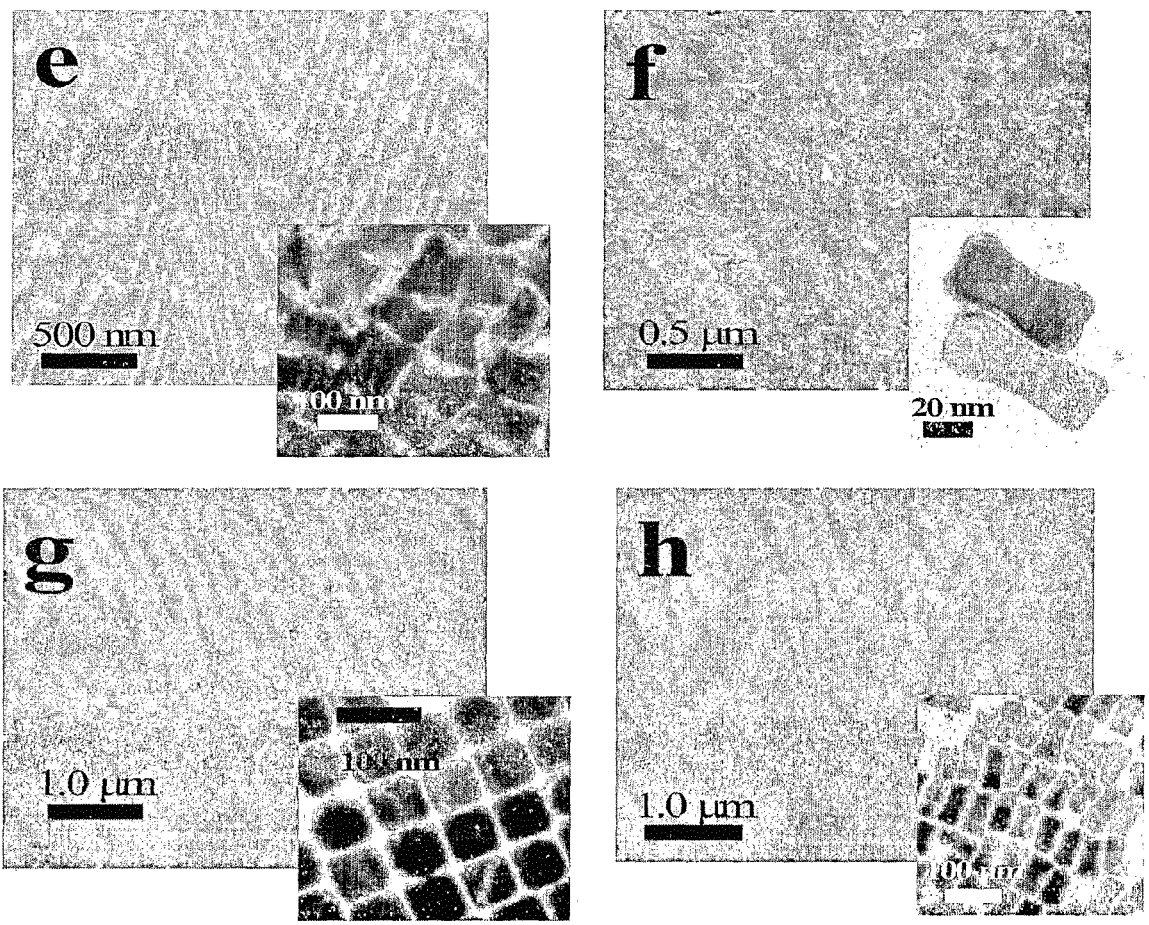

FIG. 6 shows representative SEM images of nanorods (aspect ratio 3.2, 4.4, and 16), blocks, tetrapods, dogbones, cubes and spheres immobilized on 4-MBA SAMs. Since the size of nanoparticles >100 nm, with the exception of aspect ratio 16 rods, and near the practical resolution of the instrument (~10-20 nm), it can be difficult to distinguish different shapes of nanoparticles. Therefore, TEM images of these nanoparticles are provided as insets in FIG. 6. In FIG. 6 a, aspect ratio 16 nanorods are uniformly distributed on the surface and are generally isolated, with a density of 17 rods/$\mu m^2$. This is a slightly higher density of nanorods than reported previously for 16-hexadecanoic acid SAMs. Gole, A.; Orendorff, C. J.; Murphy, C. J. *Langmuir* 2004, 20, 7117-7122. The smaller nanoparticles are well dispersed on the 4-MBA surface and number densities are calculated to be ~44 rods/$\mu m^2$ for aspect ratio 3.2 nanorods, ~38 rods/$m^2$ for aspect ratio 4.4 nanorods, ~9.5 blocks/$\mu m^2$, and 11 tetrapods/$\mu m^2$, 9 cubes/$\mu m^2$, ~32 spheres/$\mu m^2$, and ~24 dogbones/$\mu m^2$. The number density of nanoparticles is a factor in determining not only surface enhancement factors (EF), but also in comparing the SERS spectra of 4-MBA with different immobilized shapes.

Figure 7:
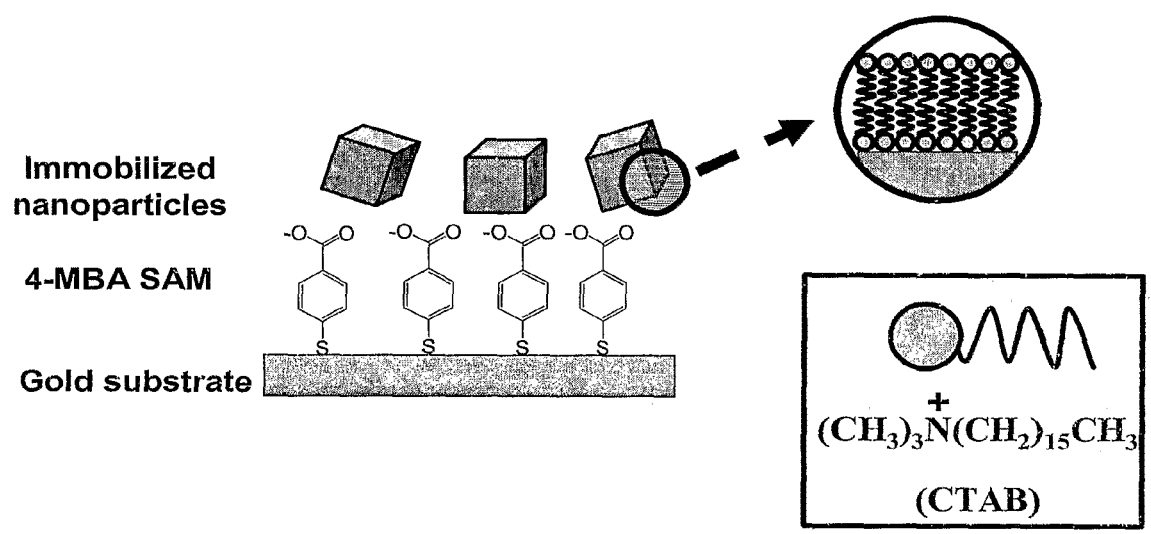
FIG. 7 shows a scheme of the nanoparticle-SAM sandwich geometry for SERS of 4-MBA.
Figure 8:
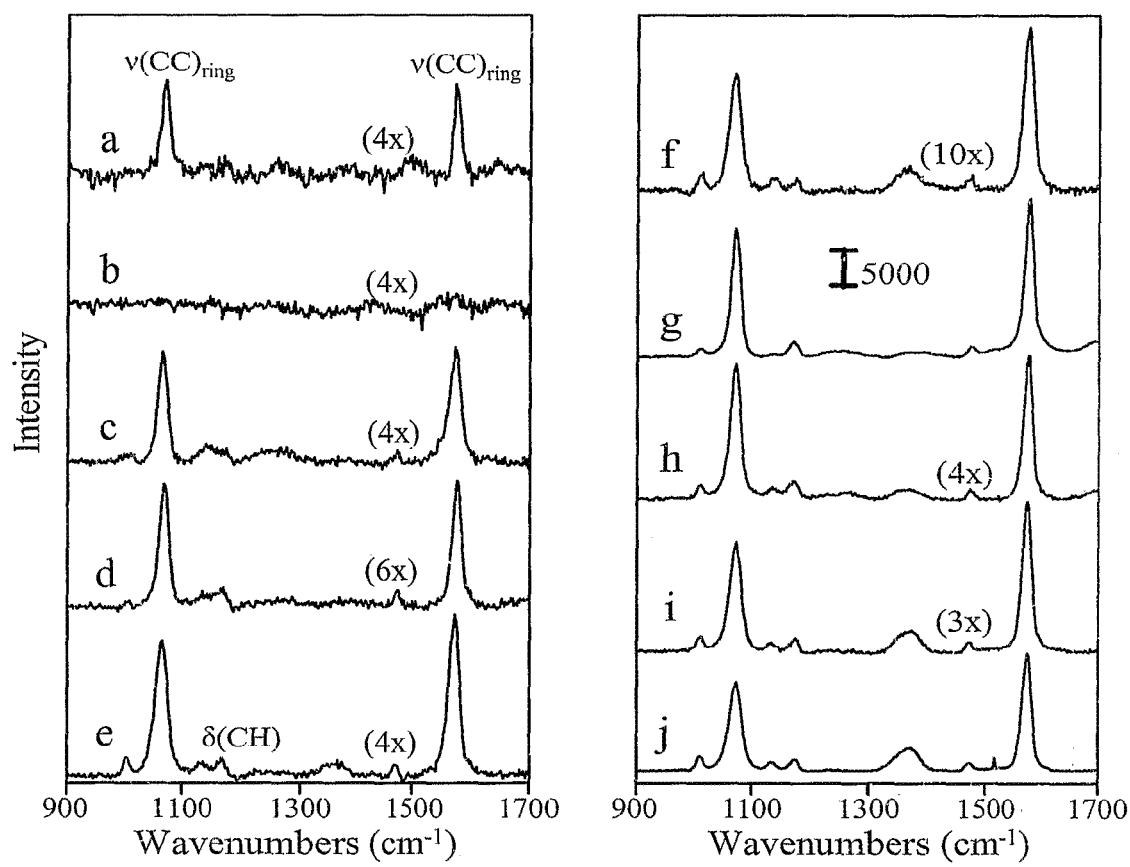
FIG. 8 shows Raman spectra of (a) 0.01 M 4-MBA and (b) 4-MBA SAM on gold, and SERS spectra of 4-MBA SAMs on gold with immobilized (c) spheres, (d) aspect ratio 3.2 rods, (e) aspect ratio 4.4 rods, (f) aspect ratio 16 rods, (g) cubes, (h) blocks, (i) tetrapods, and (j) dogbones. Integration times are (a) 300 s, (b) 480 s, (c) 300 s, (d) 120 s, (e) 120 s, (f) 30 s, (g) 30 s, (h) 30 s, (i) 30 s, and (j) 30 s.

SERS of 4-MBA SAMs using different shaped gold nanoparticles. A scheme of this sandwich geometry for acquiring SERS spectra of SAMs is shown in FIG. 7. In this architecture, the analyte molecules are SAM molecules, and are sandwiched between the smooth gold substrate and the electrostatically-immobilized gold nanocrystals. Raman spectra of 0.01 M 4-MBA alone, a 4-MBA SAM on a gold substrate with no nanoparticles, and 4-MBA SAMs on gold in the sandwich geometry with different immobilized nanocrystals are shown in FIG. 8. The corresponding peak frequency assignments are provided in Table 2. Raman spectra and SERS spectra of 4-MBA are comparable to those reported previously for 4-MBA in aqueous solution and adsorbed onto gold substrates. Michota, A.; Bukowska, J. *J. Raman Spectrosc.* 2003, 34, 21-25. Park, H.; Lee, S. B.; Kim, K.; Kim, M. S. *J. Phys. Chem.* 1990, 94, 7576-7580. Lin-Vien, J. G.; Golthup, M. B.; Fateley, W. G. Grasselli, J. G. *The Handbook of Infrared and Raman Characteristic Frequencies of Organic Molecules*; Academic Press: New York, 1991. Characteristic vibrational modes including $\nu(CC)$ ring-breathing modes (1070 and 1575 $cm^{-1}$) observed in the Raman spectra of aqueous 4-MBA and SERS spectra of 4-MBA, while other less intense modes including $\delta$ (CH) (1132 and 1173 $cm^{-1}$) and $\nu_s(COO^-)$ (1375 $cm^{-1}$) are observed in SERS spectra with immobilized nanoparticles, but are below the signal-to-noise for the Raman spectra of 0.01 M aqueous 4-MBA.

TABLE 2

| Peak Frequency ($cm^{-1}$) | | Assignment[a,b] |
|---|---|---|
| 4-MBA SAM on gold | 0.01M 4-MBA | |
| 1070 | 1073 | $\nu(CC)_{ring}$ |
| 1132 | c | $\delta(CH)$ |
| 1173 | c | $\delta(CH)$ |
| 1357 | c | $\nu_s(COO^-)$ |
| 1575 | 1575 | $\nu(CC)_{ring}$ |

[a]Assignments from references 42-44.
[b]$\delta$ = bend or deformation;
$\nu$ = stretch;
$_{ring}$ = ring breathing mode;
$^a$ = antisymmetric.
[c]Not Observed Raman spectra of aromatic thiol SAMs on smooth gold substrates has been reported previously. Taylor, C. E.; Pemberton, J. E.; Goodman, G. G.; Schoenfisch, M. H. *Appl. Spectrosc.* 1999, 53, 1212-1221. However, the instrument used in these experiments was limited to acquiring only single spectral integrations, opposed to multiple accumulations to improve the signal-to-noise ratio. No characteristic 4-MBA vibrational modes are observed in the spectra of 4-MBA SAMs on gold substrates in the absence of immobilized nanoparticles. These observations are in good agreement with those obtained by Zheng et al. for SERS of 4-ATP SAMs on silver substrates with adsorbed silver nanoparticles in the same sandwich geometry. Zheng, J.; Zhou, Y.; Li, X.; Ji, Y.; Lu, T.; Gu, R *Langmuir* 2003, 19, 632-636. In that work, characteristic vibrational bands for 4-ATP SAMs on polished silver substrates were readily observed after the immobilization of silver colloids, but were not observed for the SAMs in the absence of the colloids. Zheng, J.; Zhou, Y.; Li, X.; Ji, Y.; Lu, T.; Gu, R *Langmuir* 2003, 19, 632-636.

Surface enhancement factors (EF) are calculated for each of the different nanoparticle shapes using the following expression:

$$EF = [I_{SER}]/i[I_{Raman}] \times [M_{Bulk}]/[M_{Ads}] \quad \text{Eq. 1}$$

where $M_{Bulk}$ is the number of molecules sampled in the bulk, $M_{Ads}$ is the number of molecules adsorbed and sampled on the SERS-active substrate, $I_{SERS}$ is the intensity of a vibrational mode in the surface-enhanced spectrum, and $I_{Raman}$ is the intensity of the same mode in the Raman spectrum. For all spectra, the intensity of the $\nu(C-C)$ ring-breathing mode (~1070 $cm^{-1}$) is used to calculate EF values. Ideally, the Raman spectra of the 4-MBA SAM would be used to normalize SERS spectra in determining EF values as described by Taylor et al. Taylor, C. E.; Pemberton, J. E.; Goodman, G. G.; Schoenfisch, M. H. *Appl. Spectrosc.* 1999, 53, 1212-1221. However, as described above, instrumental limitation prevent the acquisition of interpretable Raman spectra of the 4-MBA SAM in the absence of immobilized nanoparticles. Therefore, the spectrum of aqueous 0.01 M 4-MBA is used to normalize the SERS data in the EF calculation. All spectra are normalized for acquisition time. The number of molecules sampled in the SERS experiments is determined by calculating the total two-dimensional area or "SERS footprint" occupied by the nanoparticles in the illuminated laser spot on the surface. This is approximated by multiplying the number density of nanoparticles (from the SEM images in FIG. 6), the illuminated spot size (~0.2 mm dia. at the focal point), and the nanoparticle footprint area (from the TEM images in FIG. 6) to give the total SERS surface area sampled. This number is multiplied by the bonding density of 4-MBA molecules in a SAM, ~0.5 $nmol/cm^2$ to give the total number of molecules sampled in the SERS experiments. Taylor, C. E.; Pemberton, J. E.; Goodman, G. G.; Schoenfisch, M. H. *Appl. Spectrosc.* 1999, 53, 1212-1221. It is noteworthy that there are many more molecules in the SAM that are not sandwiched between nanoparticles and the gold substrate. Taylor et al. determined the enhancement factor of smooth, vapor deposited gold substrates to be ~2 at 514.5 nm and ~64 at 720 nm. Since EF values expected for these nanoparticle-SAM samples should be several orders of magnitude greater than a factor of 64, SERS contributions from SAM molecules not sandwiched between nanoparticles and the gold substrate are assumed to be negligible.

Calculated EF values for 4-MBA SAMS with immobilized nanocrystals are given in Table 3.

TABLE 3

| Nanoparticle shape | EF |
|---|---|
| Spheres | $1.62 \pm 0.63 \times 10^7$ |
| Aspect ratio 3.2 rods | $1.02 \pm 0.40 \times 10^8$ |
| Aspect ratio 4.4 rods | $1.04 \pm 0.11 \times 10^8$ |
| Aspect ratio 16 rods | $1.08 \pm 0.08 \times 10^8$ |
| Tetrapods | $7.16 \pm 0.09 \times 10^8$ |
| Dogbones | $1.61 \pm 0.11 \times 10^9$ |
| Cubes | $2.43 \pm 0.21 \times 10^9$ |
| Blocks | $2.65 \pm 0.19 \times 10^9$ |

All EF values are between $10^7$ and $10^9$, which is significantly greater than those estimated for aromatic SAMs on rough planar substrates (~$10^6$). Taylor, C. E.; Pemberton, J. E.; Goodman, G. G.; Schoenfisch, M. H. *Appl. Spectrosc.* 1999, 53, 1212-1221. VanDuyne, R. P.; Hulteen, J. C.; Triechel, D. A. *J. Chem. Phys.* 1993, 99, 2101-2115. Likewise, these EF values are also greater than those estimated for 2-aminothiophenol adsorbed to unaggregated gold nanorods (~$10^5$) and 2,4-dinitrotoluene adsorbed on silver nanowires (~$10^5$). Nikooballht, B. Wang, J. El-Sayed, M. A. *Chem. Phys. Lett.* 2002, 366, 17-23. Tao, A.; Kim, F.; Hess, C.; Goldberger, J.; He, R.; Sun, Y.; Xia, Y, Yang, P. *Nano Lett.* 2003, 3, 1229-1323. This indicates that plasmon coupling between the nanocrystals (LSP) and the gold substrate surface (SPP) contributes to significant localized field enhancement for 4-MBA molecules in the gold nanoparticle-planar substrate sandwich, resulting in large SERS intensities. LSP-SPP coupling is believed to contribute to increase SERS intensities observed by Zhang et al. for 4-ATP SAMs on silver with immobilized silver colloids. Lyon, L. A.; Pena, D. J.; Natan, M. J. *J. Phys. Chem. B* 1999, 103, 5826-5831. However, no EF values were estimated in that work for comparison. These SERS results are comparable to those obtained by Natan and others for SPR colloid-enhanced sandwich assays, where LSP-SPP interactions contribute to SPR angle shift enhancement. Lyon, L. A.; Musick, M. D.; Natan, M. *J. Anal. Chem.* 1998, 70, 5177-5183.

While not wishing to be bound by theory, it is believed that, for these nanoparticles, enhancements are a combination of plasmon absorption, or EM contributions, and chemical effects. Cubes, blocks, and dogbones have the largest surface enhancement factors, ~$10^9$, and spheres have the smallest enhancement, $10^7$. However, cubes, blocks, and dogbones have less absorption at 633 nm than tetrapods and aspect ratio 3.2 nanorods, but still give greater Raman enhancement by a factor of 10. This indicates that differences in enhancements observed for each of these nanoparticle shapes is less dependent on resonance with the incident radiation source (EM factors) than other chemical effects.

One contributing chemical effect is the absorption strength of 4-MBA of the gold nanoparticles. El-Sayed and coworkers determined that greater Raman scattering enhancement is observed for molecules on Au {110} than Au{111}, because the Au{110} has a higher surface energy. Nikoobakht, B. Wang, J. El-Sayed, M. A. *Chem. Phys. Lett.* 2002, 366, 17-23. However, in this case the SERS analyte is immobilized in a self-assembled monolayer, and the gold nanocrystals are capped with CTAB. Therefore, chemical enhancement effects due to preferential binding of the SERS analyte to different crystal faces of the gold colloidal particles is not likely. While not wishing to be bound by theory, it is believed that the differences in EF values between nanoparticle shapes is due to the lightning rod effect. Schatz, G. C. *Acc. Chem. Res.* 1984, 17, 370-376. Gersten, J. I., *J. Chem. Phys.* 1980, 72, 5779-5780. In general, greater field enhancements are observed near the sharpest surface features. Dogbones, tetrapods, cubes, and blocks all have more well-defined edges, corners and have generally sharper surface features than rods and spheres, shown in FIG. 6. As observed here, the lightning rod effect results in greater localized field enhancement for dogbones, cubes, tetrapods, and blocks than rods, and rods having greater field enhancement than spheres.

E. CONCLUSIONS

Gold nanoparticles of various shapes and sizes are immobilized on 4-MBA SAMs on gold via electrostatic interactions, as described previously. Gole, A.; Orendorff, C. J.; Murphy, C. J. *Langmuir* 2004, 20, 7117-7122. These nanoparticle-planar substrate sandwich structures are used as SERS substrates. No vibrational bands of 4-MBA are observed in the Raman spectra of the 4-MBA SAM on sputtered gold, but vibrational bands are readily observed when gold nanoparticles of any shape are immobilized on the SAM. Results suggest that SERS of the 4-MBA SAMs in this sandwich geometry originates from plasmon coupling between localized surface plasmon of the nanoparticles and surface plasmon of the gold substrate; creating a large localized electromagnetic field enhancement, or SERS "hot spot," for the 4-MBA molecules between the nanoparticles and the planar substrate. Differences in surface enhancement are also observed for nanoparticles of different shape. Results indicate that resonance between the incident radiation and the LSP of nanoparticles, EM enhancement, is not sufficient to adequately describe differences between EF values of the various nanoparticle shapes. Chemical contributions to SERS including the surface structure and sharpness of structural features of the gold nanocrystals contribute to enhanced EF values for different shaped nanoparticles.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preparing a cetyltrimethylammonium bromide-capped gold nanoparticle comprising the steps of:
   a. providing a seed solution comprising a gold nanoparticle;
   b. providing an aqueous growth solution comprising:
      i. cetyltrimethylammonium bromide,
      ii. hydrogen tetrachloroaurate, and
      iii. ascorbic acid; and
   c. adding a quantity of the seed solution to the aqueous growth solution, thereby producing a cetyltrimethylammonium bromide-capped gold nanoparticle having a shape comprising a cube, a block, a tetrapod, a sphere, a rod, a star, or a dogbone.

2. The method of claim 1, wherein the nanoparticle has a shape comprising a cube, a block, a tetrapod, a rod with an aspect ratio of at least about 3.2, or a dogbone.

3. The method of claim 1, wherein the providing a seed solution step comprises the step of reducing hydrogen tetrachloroaurate with ascorbic acid in the presence of cetyltrimethylammonium bromide, thereby producing seeds of less than about 4 nm.

4. The method of claim 1, wherein the providing a seed solution step comprises the step of reducing hydrogen tetrachloroaurate with sodium borohydride in the presence of trisodium citrate, thereby producing seeds of from about 20 nm to about 30 nm.

5. The method of claim 1, wherein the aqueous growth solution further comprises silver nitrate.

* * * * *